(12) United States Patent
Tamarkin et al.

(10) Patent No.: US 7,483,738 B2
(45) Date of Patent: Jan. 27, 2009

(54) COMBINATION STIMULATING AND EXOTHERMIC HEATING DEVICE AND METHOD OF USE THEREOF

(75) Inventors: Dov Tamarkin, Maccabim (IL); Zvi Nitzan, Zofit (IL); Giora Arbel, Kfar Saba (IL); Daniela Mavor, Tel Aviv (IL); Yossif Gross, Moshav Mazor (IL); Shalom Luski, Rehovot (IL)

(73) Assignee: Power Paper Ltd., Petah Tikva (IL)

( * ) Notice: Subject to any disclaimer, the term of this patent is extended or adjusted under 35 U.S.C. 154(b) by 333 days.

(21) Appl. No.: 10/724,054

(22) Filed: Dec. 1, 2003

(65) Prior Publication Data

US 2004/0138712 A1 Jul. 15, 2004

Related U.S. Application Data

(60) Provisional application No. 60/429,547, filed on Nov. 29, 2002.

(51) Int. Cl.
*A61N 1/30* (2006.01)
(52) U.S. Cl. .............................. 607/3; 604/20; 604/113
(58) Field of Classification Search ...................... 607/3; 604/20, 113
See application file for complete search history.

(56) References Cited

U.S. PATENT DOCUMENTS

| | | | | |
|---|---|---|---|---|
| 4,685,911 A | * | 8/1987 | Konno et al. | 424/450 |
| 5,336,255 A | * | 8/1994 | Kanare et al. | 607/149 |
| 5,897,522 A | * | 4/1999 | Nitzan | 604/20 |
| 5,985,320 A | * | 11/1999 | Edwards et al. | 424/450 |
| 6,261,595 B1 | * | 7/2001 | Stanley et al. | 424/449 |
| 6,532,386 B2 | * | 3/2003 | Sun et al. | 604/20 |
| 6,567,696 B2 | * | 5/2003 | Voznesensky et al. | 607/3 |
| 6,890,553 B1 | * | 5/2005 | Sun et al. | 424/449 |
| 2007/0123960 A1 | * | 5/2007 | Rousmaniere | 607/96 |

* cited by examiner

*Primary Examiner*—George R Evanisko
*Assistant Examiner*—Michael Kahelin
(74) *Attorney, Agent, or Firm*—Kenyon & Kenyon LLP

(57) ABSTRACT

The present invention is of an apparatus and method for enhancing skin, muscle and nerve stimulation and controlled delivery of an active substance to a subject's skin. Moreover, the present invention is of an apparatus, featuring a combination of a stimulating device and an exothermic heating source. Preferably, the stimulating device is an iontophoretic device, or an electrical stimulation device, such as, but not limited to TENS, IFC and GC devices or a combination thereof. The present invention also provides a method of using such an apparatus for enhancing skin, muscle and nerve stimulation. Furthermore, the present invention provides a method of use of such an apparatus for enhancing controlled delivery of an active substance.

28 Claims, 1 Drawing Sheet

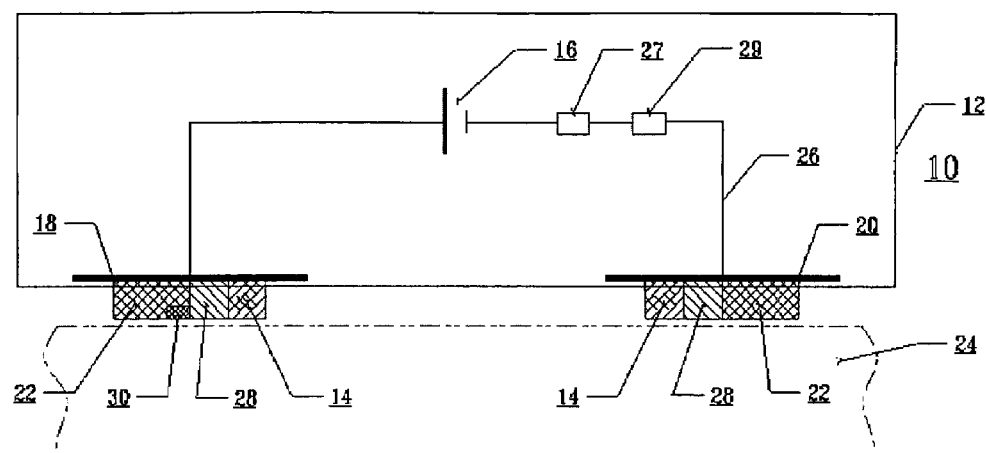
Figure I

COMBINATION STIMULATING AND EXOTHERMIC HEATING DEVICE AND METHOD OF USE THEREOF

RELATED APPLICATIONS

This application claims priority to U.S. Provisional Application No. 60/429,547, filed Nov. 29, 2002, the contents of which are incorporated herein by reference.

FIELD OF THE INVENTION

The present invention is of a device and method for enhancing skin, muscle and nerve stimulation and controlled delivery of an active substance to a subject's skin. Preferably, the present invention is of a device featuring a combination of a stimulating device and an exothermic heating source.

BACKGROUND OF THE INVENTION

Electricity has been used to treat pain for over 100 years. Electrical stimulation may directly block transmission of pain signals along nerves and has been shown to promote the release of endorphins, which are natural painkillers produced by the body. Electrical stimulation modalities of the background art include, but are not limited to: Transcutaneous Electrical Nerve Stimulation (TENS), Interferential Current (IFC) and Galvanic Stimulation (GC).

Transcutaneous electrical nerve stimulation (TENS) is a simple, non-invasive analgesic technique that is used extensively in health-care settings by physiotherapists, nurses and midwifes (Johnson, 1997; Pope, Mockett and Wright, 1995; Reeve, Menon and Corabian, 1996; Robertson and Spurritt, 1998). TENS is commonly used in the treatment of a variety of conditions, including, among others: Arthritis, Phantom limb pain following amputation, Lumbago, Post operative pain, Sports injury, Amputation, Skeletal pains, Whiplash, Rheumatoid and osteo-arthritis, menstrual (Period) pain, Pain associated with chronic fatigue syndrome, Neuralgia, Back pain, Most muscle pains and Cancer pain. Further information, defining the different aspects of TENS is provided in Mark Johnson, Transcutaneous Electrical stimulation (TENS), Chapter 17, which is incorporated herein in its entirety for background information.

Interferential current (IFC) is essentially a deeper form of TENS. In essence, IFC modulates a high frequency (4000 Hz) carrier waveform with the same signal produced by a TENS unit. The high frequency carrier waveform penetrates the skin more deeply than a regular TENS unit, with less user discomfort for a given level of stimulation. Deep in the tissues, the carrier waveform is cancelled out, resulting in a TENS-like signal deep under the skin.

Galvanic stimulation (GS) is useful in acute injuries associated with major tissue trauma, bleeding or swelling. In contrast to TENS and IFC units, which apply alternating current, galvanic stimulators apply direct current. Direct current creates an electrical field over the treated area that theoretically, changes blood flow. Galvanic stimulation can be delivered in a continuous direct current mode or in a pulse mode.

Iontophoresis is an effective and painless method of delivering cosmetic and pharmaceutical active agents to a localized tissue area by applying electrical current to a formulation of the medication. The two principal mechanisms by which electrical currents enhance molecular transport across the skin are: (a) Iontophoresis, in which a charged ion is repelled from an electrode of the same charge, and (b) Electroosmosis, the convective movement of solvent that occurs through a charged "pore" in response to the preferential passage of counter-ions when the electric field is applied.

The stimulating devices of the background art, which use TENS, IFC and GC stimulation are limited in the degree of relief these devices can provide.

There is therefore a need for an apparatus and method, such as is disclosed in the present invention, to provide an improved stimulating apparatus, for better, more effective treatment.

SUMMARY OF THE INVENTION

The present invention is of an apparatus and method for enhancing the skin, muscle and nerve stimulation and controlled delivery of an active substance to a subject's skin. Moreover, the present invention is of an apparatus, featuring a combination of a stimulating device and an exothermic heating source. Preferably, the stimulating device is an iontophoretic device, or an electrical stimulation device, such as, but not limited to TENS, IFC and GC, or a combination thereof. The present invention also provides a method of using such an apparatus for enhancing skin, muscle and nerve stimulation. Furthermore, the present invention provides a method of use of such an apparatus for enhancing controlled delivery of an active substance.

In a first embodiment the present invention provides a combination exothermic heating and stimulating apparatus including (a) a stimulating device for providing current stimulation of an anatomical element, wherein the stimulating device includes (i) a power supply for powering the stimulating device; (ii) at least one positive electrode, connected to the power supply; and (iii) at least one negative electrode, connected to the power supply, wherein the electrodes are for conducting current to the anatomical element; and (b) an exothermic heating component for heating the anatomical element.

In a preferred embodiment the stimulating device is an iontophoretic device.

In a preferred embodiment the stimulating device is an electrical stimulation device.

In a preferred embodiment the electrical stimulating device is selected from the group consisting of transcutaneous electrical nerve stimulation device, interferential current stimulation device and galvanic stimulation device.

In a preferred embodiment the exothermic heating component is a mixture of oxidizable material and carbon or activated carbon powder.

In a preferred embodiment the exothermic heating component is contained in a hydrogel.

In a preferred embodiment the combination exothermic heating and stimulating apparatus is for use in the treatment of a dermatological disorder.

In a preferred embodiment the stimulating device includes an iontophoretic device and an electrical stimulation device.

In a preferred embodiment the combination exothermic heating and stimulating apparatus is for use in the treatment of a condition, which is responsive to drug treatment and is associated with pain.

In a preferred embodiment the stimulating device is an iontophoretic device and an electrical stimulating device for readily facilitating monophasic pulse current and non-equal biphasic alternating current.

In a preferred embodiment the electrical stimulating device is for readily facilitating monophasic pulse current is selected from the group consisting of, TENS device, interferential current stimulation device and galvanic stimulation device.

In a preferred embodiment the power supply is a thin layer electrochemical cell.

In a preferred embodiment the thin layer electrochemical cell is a flexible thin layer liquid state electrochemical cell which includes a first layer of insoluble negative pole, a second layer of insoluble positive pole and a third layer of aqueous electrolyte, the third layer being disposed between the first and second layers.

In a preferred embodiment the flexible thin layer liquid state electrochemical cell is an open cell, and further wherein the third layer includes: (i) a deliquescent material for keeping the open cell wet at all times; (ii) an electroactive soluble material for obtaining required ionic conductivity; and (iii) a water soluble polymer for obtaining a required viscosity for adhering the first and second layers to the third layer.

In a preferred embodiment the anatomical part is selected from the group consisting of skin, nerve, joint and flexor, bone and muscle.

In a second embodiment the present invention provides a combination exothermic heating and stimulating apparatus including (a) an iontophoresis device for providing controlled delivery of a drug and current stimulation of an anatomical element, wherein the iontophoresis device includes (i) a power supply for powering the iontophoresis device; (ii) at least one positive electrode, connected to the power supply; and (iii) at least one negative electrode, connected to the power supply, wherein the electrodes are for conducting current to the anatomical element; and (b) an exothermic heating component for heating the anatomical element.

In a third embodiment the present invention provides a combination exothermic heating and stimulating apparatus including (a) an electrical stimulating device for providing current stimulation of an anatomical element, wherein the electrical stimulating device includes (i) a power supply for powering the stimulating device; (ii) at least one positive electrode, connected to the power supply; and (iii) at least one negative electrode, connected to the power supply, wherein the electrodes are for conducting current to the anatomical element; and (b) an exothermic heating component for heating the anatomical element. Preferably, the electrical stimulating device is selected from the group consisting of transcutaneous electrical nerve stimulation device, interferential current stimulation device and galvanic stimulation device.

In a fourth embodiment the present invention provides a combination exothermic heating and stimulating apparatus including: (a) an electrical stimulating device for providing current stimulation of an anatomical element, wherein the electrical stimulating device includes: (i) a power supply for powering the stimulating device; (ii) at least one positive electrode, connected to the power supply; and (iii) at least one negative electrode, connected to the power supply, wherein the electrodes are for conducting current to the anatomical element and for iontophoretic delivery of an active substance; and (b) an exothermic heating component for heating the anatomical element. Preferably, the apparatus is for providing combination exothermic heating, electrical stimulation and iontophoretic stimulation and active substance delivery.

In a preferred embodiment the current is selected from the group consisting of monophasic pulse current and non-equal biphasic alternating current.

In a fifth embodiment the present invention provides a method for treating a condition responsive to drug therapy and associated with pain including the steps of: (a) providing a combination exothermic heating and stimulating apparatus wherein the apparatus includes, (i) a stimulating device for providing current stimulation of skin, wherein the stimulating device includes a. a power supply for powering the stimulating device; b. at least one positive electrode, connected to the power supply; and c. at least one negative electrode, connected to the power supply, wherein the electrodes are for conducting current to the skin; and (ii) an exothermic heating component for heating the skin; (b) providing exothermic stimulation of the skin area; (c) providing electrical stimulation of the skin area; (d) administering an active substance by iontophoresis to the skin area; and (e) maintaining the exothermic stimulation, electrical stimulation and the iontophoretic administration for a period of time.

In a preferred embodiment the electrical stimulation is interferential current stimulation. Preferably, the interferential current stimulation includes providing frequency modulation of about 4000 Hz.

In a preferred embodiment the electrical stimulation is galvanic stimulation.

In a preferred embodiment the electrical stimulation is monophasic pulse current TENS.

In a preferred embodiment the iontophoretic administration is substantially contemporaneous with the exothermic stimulation.

In a preferred embodiment the exothermic stimulation precedes the iontophoretic administration.

In a preferred embodiment the exothermic stimulation is after the iontophoretic administration.

In a preferred embodiment the condition responsive to drug therapy and associated with pain is selected from the group consisting of general localized pain, joint pain, muscle pain, back pain, rheumatic pain, arthritis, wound treatment and osteoarthritis and combinations thereof.

In a sixth embodiment the present invention provides a method for treating alleviating or preventing a dermatological disorder, including the steps of: (a) providing topical exothermic stimulation of a skin area; (b) administrating the active substance iontophoretically to the skin area; and (c) maintaining the exothermic stimulation and the iontophoretic administration for a period of time.

In a preferred embodiment the treatment is directed to a disease etiology selected from the group consisting of bacterial, fungal, viral, parasitic, inflammatory, autoimmune, allergic, hormonal, malignant and combinations thereof.

In a preferred embodiment the dermotological disorder is selected from the group of cosmetic disorders consisting of cracked skin, wrinkles, scars, hyperpigmentation, melasma, chlosama, freckles, excessive suntan, hypopigmentation, puffy eyes, cellulite, obesity, skin redness and telangiectasia.

The term 'pain' as used herein shall include, but will not be limited to an unpleasant sensory and emotional experience associated with actual or potential tissue damage, or described in terms of such damage. The term includes pain peripheral or central in origin. Peripheral pain originates in muscles, tendons, etc., or in the peripheral nerves themselves. Pain originating in the peripheral nerves, i.e. via trauma to the nerves, is neurogenic pain. Central pain arises from central nervous system pathology. Most of it is due to structural changes in the CNS, e.g., spinal cord injury, multiple sclerosis, stroke and epilepsy. Nociceptive pain is pain in which normal nerves transmit information to the central nervous system about trauma to tissues. Neuropathic pain is pain in which there are structural and/or functional nerve damage.

The term 'drug' as used herein shall include, but will not be limited to electrical stimulation, ionohoretic stimulation and any other suitable means of excitation of a anotomical element, such as a muscle, nerve, skin, joint, flexor, bone and organ.

The term 'stimulate' as used herein shall include, but will not be limited to, electrical stimulation, iontophoretic stimulation and any other suitable means of excitation of an anatomical element, such as a muscle, nerve, skin, joint, flexor, bone and organ.

The term 'anatomical element' as used herein shall include, but will not be limited to, any part of an animal or human body, such as, but not limited to an organ, muscle, nerve, joint, flexor and skin.

The term 'anatomical element' as used herein shall include, but will not be limited to any part of an animal or human body, such as, but not limited to an organ, muscle, nerve, joint, flexor and skin.

The term 'active substance' as used herein shall include, but will not be limited to a drug, part of a drug or prodrug, which contains or is a drug part, which is effective or anticipated to be effective in the treatment, prevention or diagnosis of disease. The term includes any suitable type of composition, formulation or dose.

BRIEF DESCRIPTION OF THE DRAWINGS

With reference now to the drawing in detail, it is stressed that the particulars shown, are by way of example and for the purposes of illustrative discussion of the preferred embodiment of the present invention only, and are presented for providing what is believed to be the most useful and readily understood description of the principles and conceptual aspects of the invention. In this regard, no attempt is made to show structural details of the invention in more detail than is necessary for a fundamental understanding of the invention, the description taken with the drawing making apparent to those skilled in the art how the several forms of the invention may be embodied in practice.

FIG. 1 shows a schematic view of a preferred embodiment of the combination exothermic heating and stimulation apparatus of the present invention.

DETAILED DESCRIPTION OF THE PREFERRED EMBODIMENTS

The present invention is of an apparatus and method for enhancing skin, muscle and nerve stimulation and controlled delivery of an active substance to a subject's skin. Moreover, the present invention is of an apparatus, featuring a combination of a stimulating device and an exothermic heating source. Preferably, the stimulating device is an iontophoretic device, or an electrical stimulation device, such as, but not limited to TENS, IFC and GC devices or a combination thereof.

The present invention also provides a method of using such an apparatus for enhancing skin, muscle and nerve stimulation. Furthermore, the present invention provides a method of use of such an apparatus for enhancing controlled delivery of an active substance.

The principles and operation of systems according to the present invention may be better understood with reference to the figure. The figure shows one embodiment of the present invention and is not limiting.

FIG. 1 shows a schematic view of a preferred embodiment of the combination exothermic heating and stimulation apparatus 10, wherein the apparatus of the present invention 10 features a stimulating device 12 and an exothermic heating component 14. As can be seen in FIG. 1, stimulating device 12, preferably includes a power source 16 for providing power to the apparatus of the present invention 10, at least one positive electrode 18 and at least one negative electrode 20, electrodes 18 and 20 for conducting current through a conducting material 22 into anatomical element 24, such as skin 24 of a subject and circuitry 26.

Optionally, stimulating device 12, is an iontophoresis device 12, or an electrical stimulation device 12, or a combination of an iontophoresis device 12 and an electrical stimulation device 12.

In a preferred embodiment, wherein stimulating device 12 is an electrical stimulation device 12, electrical stimulation device 12 may be any electrical stimulation device 12 known to those skilled in the art that is consistent with the principles of the invention. Such device 12 may include electrical stimulation modalities, selected from the group of transcutaneous electrical nerve stimulation (TENS) 12, interferential current (IFC) 12 and galvanic stimulation (GC) 12. For each of these modalities, device 12 includes an electronic circuit 26, capable of producing the desirable mode of stimulation, i.e., direct or alternating current, pulse frequency (when applicable), pulse duration and voltage. Optionally, circuitry includes a DC-DC converter 27 for readily facilitating increasing voltage or/and a DC-AC 29 converter. AC is optionally monophasic or biphasic.

Optionally, wherein stimulating device 12 is an iontophoretic device 12, iontophoretic device 12 may be any iontophoretic device 12 known to those skilled in the art that is consistent with the principles of the invention. Preferably, iontophoretic device 12 is iontophoretic device 12 disclosed in U.S. Pat. No. 5,897,522, which discloses a transdermal patch adapted for iontophoretic delivery of an active substance into the skin. U.S. Pat. No. 5,897,522, discloses an active pad having two electrodes connected to a power source. The power source is disclosed to be a flexible battery for generating the iontophoresis, ultrasound or electroporation effects. These effects activate and effectively deliver the active substance through the skin. The active patch can also be used to recover a compound from the body's surface. In one embodiment, the active pad has a surface adapted to adhere to the body of the patient for delivering or absorbing active substances therefrom. In another embodiment, the active pad is equipped with the required electronics and/or an ultrasound generator.

Optionally, wherein stimulating device 12 is a combination electrical stimulating device 12 and iontophoresis device 12, electrical stimulation device 12 is any electrical stimulation device 12, which can be used to provide iontophoresis. Preferably, electrical stimulating device 12 is a monophasic pulse current device or a non-equal biphasic AC device. Equal biphasic AC TENS can not be used for iontophoresis. Power source 16 activates electrical stimulating device 12, and the resulting current flow can be employed for iontophoretic stimulation and delivery.

Optionally, power source 16 of the present invention may be any power source 16 known to those skilled in the art that is consistent with the principles of the invention. Preferably, power source 16 is a thin and flexible battery 16 adapted to be used with a flexible patch (not shown in FIG. 1). More preferably, power source 16 is a thin and lightweight battery 16. Batteries 16 weighing less than about 100 gr. are preferable, even more preferable are batteries 16 weighing less than about 10 gr. Most preferable are batteries 16 weighing less than about 2 gr.

One example of a preferred battery 16 is disclosed in U.S. Pat. Nos. 5,652,043, 5,811,204 and 5,897,522 to Nitzan, which are directed to a flexible thin layer open electrochemical cell 16 and applications thereof. As disclosed in these patents, an exemplary embodiment of a flexible thin layer open electrochemical cell 16 includes an electrochemical cell 16 having a first layer of insoluble negative pole, a second layer of insoluble positive pole and a third layer of aqueous electrolyte; the third layer being disposed between the first and the second layers and including (a) a deliquescent material for keeping the open cell wet at all times; (b) an electroactive soluble material for obtaining required ionic conductivity; and (c) a water soluble polymer for adhering the first and the second layers to the third layer.

Preferably, electrodes 18 and 20 are electrically connected to power supply 16, using well known means, such as but not limited to, printed flexible circuits, metal foils, wires, electrically conductive adhesives or by direct contact. Contact between electrodes 18 and 20 and between each of electrodes 18 and 20 and the opposite pole layer is prevented. Preferably, electrodes 18 and 20 are electrically conductive and may be formed of any suitable material, such as, but not limited to metals, aluminum, platinum, stainless steel, gold and titanium, hydrophobic polymer matrix containing a conductive filler such as metal powder/flakes, powdered graphite, carbon fibers or other known electrically conductive filler material. Optionally, each of electrodes 18 and 20 may be of any size and shape and located with respect to one another in any arrangement as may be required to cover the body/skin 24 portion under treatment.

Optionally, exothermic heating component 14 of the apparatus of the present invention 10 may be any exothermic heating component 14 known to those skilled in the art that is consistent with the principles of the invention. Preferably, heating component 14 is configured and controlled to provide heat of anatomical element 24, such as skin 24, wherein anatomical element 24 is not heated to a temperature higher than about 42° C. Optionally, any suitable amount of exothermic heating component 14 is used and can be dependent on the severity and condition to be treated.

For example, U.S. Pat. No. 6,465,709 to Sun et al., which is incorporated herein in its entirety for background information, discloses an exothermic heating component 14 including a heat generating layer which includes a mixture of oxidizable material and carbon or activated carbon powder. Examples of oxidizable metal powders include, among others, iron, aluminum, magnesium, zinc and a mixture thereof. The heat-generating layer also contains electrolytes/salts. The electrolytes/salts include, among others, salts of sodium, potassium, lithium, calcium, iron, magnesium and aluminum. Examples of electrolytes include, among others, NaCl, KCl, LiCl, $CaCl_2$, $FeCl_3$, $FeCl_2$, $MgCl_2$, $AlCl_3$, $Na_2SO_4$, $K_2SO_4$, $Fe(SO_4)_3$, $FeSO_4$, or $MgSO_4$.

A further optional example of an exothermic heating component 14 is disclosed in, U.S. Pat. No. 4,114,591 to Nakagawa, which is also incorporated herein in its entirety for background information. U.S. Pat. No. 4,114,591 describes an exothermic heating component including an exothermic metallic composition that can be used as a body warmer. The composition includes (1) one or more members selected from the group including iron, aluminum and magnesium in the form of fine particle and (2) an oxidation agent including one or more members selected from the group including ferrosoferric oxide, plumboblumbic oxide, trimanganese tetroxide, black copper oxide and manganese dioxide in the form of fine particle, water and particulate oxidation assistants such as sodium chloride and active carbon. When oxidation agent and the principal metallic components are placed together in the presence of air the oxidation reaction takes place releasing heat. The rate of the exothermic reaction can be controlled by controlling the air supply, for example, by containing the mixture in a porous bag that has a low permeability of air.

A still further optional example of an exothermic heating component 14 is disclosed in U.S. Pat. No. 6,328,761 to Ueki, which is also incorporated herein in its entirety for background information. U.S. Pat. No. 6,328,761 discloses an exothermic heating component including a disposable body warmer having an exothermic composition capable of generating heat in the presence of air. The body warmer is generally shown to have the shape of a planar substrate. The exothermic composition includes metal powder such as iron (preferably metal powder treated with sulfur or a sulfur-containing compound), activated carbon, water, a water-retaining material (powdery wood, vermiculite, diatomaceous earth, pearlite, silica gel, alumina, water-absorptive resin or the like) and common salts. The exothermic composition is placed in a container having air-permeable and air-impermeable surfaces. The exothermic composition is activated through exposure to air or water.

Exothermic heating component 14 and stimulating device 12, such as electrical stimulation device 12, or iontophoretic device 12 of the apparatus of the present invention 10 can optionally be connected to, integrally formed with, partially formed with, or disposed in many different ways, to one another.

In one embodiment, exothermic heating component 14 is optionally integrated with the iontophoretic device 12. In such an embodiment, exothermic heating component 14 can optionally be a sheet or a planar surface and electrical stimulating device 12 or iontophoretic device 12 can optionally have the form of a dermal patch. In a preferred embodiment the dermal patch can adhere to and conform to a human body for an extended wear and use. According to this embodiment, exothermic heating component 14 can be interposed between the patient's skin and the dermal patch.

In another embodiment, exothermic heating component 14 may include an exothermic material 28, which is topically applied to skin 24 at the desired location. In this embodiment, stimulating device 12 is placed over subject's skin 24 where exothermic material 28 has been topically administered (not shown in FIG. 1).

In yet another embodiment, wherein stimulating device 12 is or includes iontophoresis device 12, exothermic heating component 14 may optionally include exothermic material 28 that is combined with active substance 30 to be administered and is activated by applying the dermal patch (not shown in FIG. 1). In this embodiment, exothermic material 28 is activated when iontophoretic device 12 is activated.

Optionally, exothermic heating component 14 is contained or mixed in conducting medium 22, such as, but not limited to hydrogel 14 or gel 14, (shown in FIG. 1) which is in contact with skin 24. Preferably, conductive medium 22 is for providing an electrical interface on body/skin 24 for electrodes 18 and 20.

The apparatus of the present invention 10 utilizes the synergistic effect of combining exothermic heating component 14, which readily facilitates providing heat to underlying skin 24 with, stimulation, such as electrical stimulation, or, iontophoresis that delivers active substance 30 into skin 24, or a combination thereof. Combining heat from component 14 and electrical stimulation from device 12 affords a synergistic muscle and nerve stimulation and relaxation effect and has the potential to improve pain relief. Likewise, combining heat from component 14 with iontophoretic device 12 can greatly enhance delivery of active substance 30 into skin 24.

In one preferred embodiment, the invention is preferably directed to the combination exothermic heating and stimulating apparatus 10 including iontophoretic device 12 and exothermic heating component 14. This combination synergistically increases the delivery of active substance 30 into skin 24.

Without being bound to any particular mechanism of operation, it is envisioned that the synergistic effect can be achieved in at least one of the following ways. Firstly, warming of subject's skin 24 improves the blood circulation rate at the skin surface, and thereby increases amount of active substance 30 that is delivered to the circulatory system by increasing the concentration gradient between iontophoretic device 12 and the circulatory system. Secondly, warming subject's skin 24 also opens pores in skin 24, and thereby improves the delivery of active substance 30 into skin 24. Thirdly, warming subject's skin 24 melts the lipids in skin 24 that might otherwise impede the delivery of active substance 30 into skin 24. Fourthly, warming subject's skin 24 generally increases the speed at which molecules are moving in skin 24, and thereby increases the speed at which active substance 24 is delivered into skin 24. Fifthly, it is considered that heating of subject's skin 24 contributes to skin conditioning through (i) warming up the tissue, (ii) stimulating the blood circulation at that location, and (iii) opening the skin pores. These effects are important for increasing the delivery of an active substance 30 in general, and a cosmetic substance 30 in particular, to the skin. Sixthly, heating skin 24 is deemed to contribute to the muscle and nerve relaxation.

Preferably, the apparatus of the present invention 10, has medical and cosmetic application. As a result of the synergistic effect of combination treatment, whereby more than one mechanism, pathway or factors involved in a condition are treated, it is envisioned that more of the population will be responsive to treatment.

The combination of iontophoresis device 12 and exothermic heating component 14 as is provided in one embodiment of the present invention, acts synergistically to induce improved alleviation of the symptoms of various disorders. In the case of optionally including an appropriate active agent 30 in a preparation, applied to skin 24 in intimate contact with the combination of iontophoresis device 12 and exothermic heating component 14, apparatus 10 is useful in the treatment of a variety of dermatological disorders. Examples of dermatological disorders, include but are not limited to dermatitis, Contact dermatitis, Atopic Dermatitis, Seborrheic Dermatitis, Nummular Dermatitis, Chronic Dermatitis Of The Hands And Feet, Generalized Exfoliative Dermatitis, Stasis Dermatitis, Lichen Simplex Chronicus, Bacterial Infections, Cellulitis, Acute Lymphangitis, Lymphadenitis, Erysipelas, Cutaneous Abscesses, Necrotizing Subcutaneous Infections, Staphylococcal Scalded Skin Syndrome, Folliculitis, Furuncles, Hidradenitis Suppurativa, Carbuncles, Paronychial Infections, Erythrasma, Fungal Infections, Dermatophyte Infections, Yeast Infections, Parasitic Infections, Scabies, Pediculosis, Creeping Eruption, Viral Infections, Disorders of Hair Follicles and Sebaceous Glands, Acne, Rosacea, Perioral Dermatitis, Hypertrichosis, (Hirsutism), Alopecia, Pseudofolliculitis Barbae, Keratinous Cyst, Scaling Papular Diseases, Psoriasis, Pityriasis Rosea, Lichen Planus, Pityriasis Rubra Pilaris, Benign Tumors, Moles, Dysplastic Nevi, Skin Tags, Lipomas, Angiomas, Pyogenic Granuloma, Seborrheic Keratoses, Dermatofibroma, Keratoacanthoma, Keloid, Malignant Tumors, Basal Cell Carcinoma, Squamous Cell Carcinoma, Malignant Melanoma, Paget's Disease Of The Nipples, Kaposi's Sarcoma, Reactions To Sunlight, Sunburn, Chronic Effects of Sunlight, Photosensitivity, Bullous Diseases, Pemphigus, Bullous Pemphigoid, Dermatitis Herpetiformis, Linear Immunoglobulin A Disease, Pigmentation Disorders, Hypopigmentation, Vitiligo, Albinism, Postinflammatory hypopigmentation, Hyperpigmentation, Melasma (chloasma), Drug-induced hyperpigmentation, Postinflammatory hyperpigmentation, Disorders of Cornification, Ichthyosis, Keratosis Pilaris, Calluses And Corns, Actinic keratosis, Pressure Sores, Disorders of Sweating, Inflammatory reactions, Drug Eruptions, Toxic Epidermal Necrolysis, Erythema Multiforme, Erythema Nodosum, Granuloma Annulare.

In a preferred embodiment of the combined exothermic heating and stimulating apparatus 10, exothermic heating component 14 and iontophoresis device 12 can optionally be used with a suitable active agent 30 applied to skin 24 in intimate contact with the apparatus of the present invention 10 to treat, for example, dry skin, cracked skin, wrinkles, scars, hyperpigmentation, melasma, chlosama, freckles, excessive suntan, hypopigmentation, puffy eyes, cellulite, obesity, skin redness and telangiectasia.

In addition, in a preferred embodiment of the combined exothermic heating and stimulating apparatus 10, exothermic heating component 14 and iontophoresis device 12 can optionally be used with a suitable active agent 30 applied to skin 24 in intimate contact with the apparatus of the present invention 10 in the treatment of non-dermatological disorders, which respond to transdermal delivery of an active agent 30. By way of example, such disorders include, but are not limited to localized pain in general, as well as joint pain, muscle pain, back pain, rheumatic pain, arthritis, osteoarthritis, conditions, which respond to hormone therapy, such as hormone replacement therapy, transdermal nicotine administration, and other respective disorders, known in the art of drug delivery.

In a preferred embodiment of the combined exothermic heating and stimulating apparatus 10, including exothermic heating component 14 and electrical stimulating device 12, apparatus 10 can optionally be used to synergistically induce the alleviation of pain, associated for example with arthritis, lumbago, post operative pain, sports injury, amputation, skeletal pains, whiplash, rheumatoid and osteo-arthritis, pain associated with chronic fatigue syndrome, back pain and muscle pains.

Furthermore, in a preferred embodiment of the combined exothermic heating and stimulating apparatus 10, including exothermic heating component 14, iontophoresis device 12 and electrical stimulating device 12, apparatus 10 can optionally be used with a suitable active agent 30 for the simultaneous treatment of dermatological and non-dermatological disorders as shown above and in pain management. Preferably, the apparatus 10, can be used for the treatment of conditions associated with pain and responsive to drug treatment. Examples of such conditions, include, but are not limited to, localized pain in general, as well as joint pain, muscle pain, back pain, rheumatic pain, arthritis, wound treatment and osteoarthritis. The apparatus of the present invention 10 provides an apparatus, which is advantageous, eliminating the need for two separate treatments, for a condition, which is drug responsive and associated with pain.

A method for treating, alleviating, or preventing a condition responsive to iontophoretic drug therapy (such as, but not limited to conditions listed above) includes the steps of providing a combination exothermic heating and stimulating apparatus 10 of the present invention, wherein stimulating device 12 is an iontophoretic device 12. Anatomical element 24, such as skin area 24 to be treated is heated with exothermic heating component. Subsequently, active substance is administered by iontophoresis into warmed anatomical element 24, such as skin 24. Heating of anatomical element 24, such as skin 24 and iontophoretic stimulation and administration is maintained for a period of time, which depends on the condition being treated and its severity. Optionally, heating of skin 24 may not occur before iontophoresis, but at the same time or after iontophoresis.

A method for treating, alleviating, or preventing a condition, responsive to electrical stimulation (such as, but not limited to conditions listed above) includes the steps of providing a combination exothermic heating and stimulating apparatus 10 of the present invention, wherein stimulating device 12 is an electrical stimulating device 12. Anatomical element 24, such as skin area 24 to be treated is heated with exothermic heating component. Subsequently, electrical stimulating device 12 is activated to stimulate warmed anatomical element 24, such as skin 24. Heating of anatomical element 24, such as skin 24 and electrical stimulation is maintained for a period of time, which depends on the condition being treated and its severity. Optionally, heating of skin 24 may be initiated after electrical stimulation, or at the same time as electrical stimulation.

A method for treating, alleviating, or preventing a condition responsive to iontophoretic drug therapy (such as, but not limited to conditions listed above) and electrical stimulation includes the steps of providing a combination exothermic heating and stimulating apparatus 10 of the present invention, wherein stimulating device 12 is an iontophoretic device 12 and an electrical stimulating device 12, which preferably applies monophasic pulse current or non-equal biphasic AC. Anatomical element 24, such as skin area 24 to be treated is heated with exothermic heating component. Subsequently, skin 24 is stimulated with electrical stimulation device 12 and active substance 30 is administered by iontophoresis into warmed anatomical element 24, such as skin 24. Heating of anatomical element 24, such as skin 24, iontophoretic stimulation and administration of active substance 30 and electrical stimulation is maintained for a period of time, which depends on the condition being treated and its severity. Optionally, heating of skin 24 may be initiated after or at the same time as iontophoresis and electrical stimulation.

While the principles of the invention have been discussed in relation to exemplary embodiments discussed herein, it is understood that the principles of the invention are not limited thereto.

It is to be understood that the invention is not limited in its application to the details of construction and the arrangement of the components set forth in the description. The invention includes other embodiments and can be practiced or implemented in various ways. Also it is to be understood that the phraseology and terminology employed herein is for the purpose of description only and should not be regarded as limiting.

What is claimed is:

1. A combination exothermic heating and stimulating apparatus having a side for application to an anatomical element, the apparatus comprising:
   (a) a stimulating device for providing current stimulation of the anatomical element, wherein the stimulating device comprises: (i) a power supply for powering the stimulating device; (ii) at least one positive electrode, connected to the power supply; and (iii) at least one negative electrode, connected to the power supply, wherein the at least one electrodes are for conducting current to the anatomical element; and
   (b) an exothermic heating component for heating the anatomical element, wherein the exothermic heating component is contacted with the side and is adapted to directly contact the anatomical element.

2. The combination exothermic heating and stimulating apparatus of claim 1, wherein the stimulating device is an iontophoretic device.

3. The combination exothermic heating and stimulating apparatus of claim 1, wherein said stimulating device is an electrical stimulation device.

4. The combination exothermic heating and stimulating apparatus of claim 3, wherein said electrical stimulation device is selected from the group consisting of transcutaneous electrical nerve stimulation device, interferential current stimulation device and galvanic stimulation device.

5. The combination exothermic heating and stimulating apparatus of claim 1, wherein said stimulating device is an electrical stimulating device and an iontophoretic device.

6. The combination exothermic heating and stimulating apparatus of claim 5, for use in the treatment of a condition, which is responsive to drug treatment and is associated with pain.

7. The combination exothermic heating and stimulating apparatus of claim 5, wherein said stimulating device is an iontophoretic device and an electrical stimulating device for readily facilitating monophasic pulse current and non-equal biphasic alternating current.

8. The combination exothermic heating and stimulating apparatus of claim 7, wherein said electrical stimulating device for readily facilitating monophasic pulse current is selected from the group consisting of TENS device, interferential current stimulation device and galvanic stimulation device.

9. The combination exothermic heating and stimulating apparatus of claim 1, wherein the exothermic heating component is a mixture of oxidizable material and carbon or activated carbon powder.

10. The combination exothermic heating and stimulating apparatus of claim 1, wherein the apparatus further comprises a hydrogel and wherein the exothermic heating component is contained in the hydrogel.

11. A method of treating a dermatological disorder comprising applying the combination exothermic heating and stimulating apparatus of claim 1 to the anatomical element, wherein the anatomical element is skin.

12. The combination exothermic heating and stimulating apparatus of claim 1, wherein the power supply is a thin layer electrochemical cell.

13. The combination exothermic heating and stimulating apparatus of claim 12, wherein the thin layer electrochemical cell is a flexible thin layer liquid state electrochemical cell which includes a first layer of insoluble negative pole, a second layer of insoluble positive pole and a third layer of aqueous electrolyte, the third layer being disposed between the first and second layers.

14. The combination exothermic heating and stimulating apparatus of claim 13, wherein the flexible thin layer liquid state electrochemical cell is an open cell, and further wherein the third layer includes: (i) a deliquescent material for keeping the open cell wet at all times; (ii) an electroactive soluble material for obtaining required ionic conductivity; and (iii) a water soluble polymer for obtaining a required viscosity for adhering the first and second layers to the third layer.

15. The combination exothermic heating and stimulating apparatus of claim 1, wherein the anatomical element is selected from the group consisting of skin, nerve, joint, flexor, bone and muscle.

16. A combination exothermic heating and stimulating apparatus having a side for application to an anatomical element, the apparatus comprising: (a) an iontophoresis device for providing controlled delivery of a drug and current stimulation of the anatomical element, wherein the iontophoresis device comprises: (i) a power supply for powering the iontophoresis device; (ii) at least one positive electrode, connected to the power supply; and (iii) at least one negative electrode, connected to the power supply, wherein the at least one electrodes are for conducting current to the anatomical element; and (b) an exothermic heating component for heating the anatomical element, wherein the exothermic heating component is contacted with the side and is adapted to directly contact the anatomical element.

17. The combination exothermic heating and stimulating apparatus of claim 1, wherein the apparatus is for use in the treatment of at least one or a combination of pain management, localized pain, joint pain, muscle pain, whiplash, lumbago, post-operative pain, sports injury, amputation, skeletal pain, back pain, rheumatic pain, arthritis, wound treatment and rheumatoid and osteo arthritis and chronic fatigue syndrome pain.

18. The combination exothermic heating and stimulating apparatus of claim 1, wherein the apparatus is for use in the treatment of a fungal infection.

19. The combination exothermic heating and stimulating apparatus of claim 18, wherein the apparatus is for use in the treatment of a dermatophyte infection and/or yeast infection and/or paronychial infection.

20. The combination exothermic heating and stimulating apparatus of claim 1, wherein the exothermic heating component is at least one of connected to, integrally formed, integrated or partially formed with the stimulating device.

21. The combination exothermic heating and stimulating apparatus of claim 1, wherein the exothermic heating component is adapted to be topically applied to the anatomical element.

22. The combination exothermic heating and stimulating apparatus of claim 1 further comprising an active substance to be delivered and wherein the exothermic heating component is combined with the active substance that is to be delivered.

23. The combination exothermic heating and stimulating apparatus of claim 2, wherein the exothermic heating component is activated by at least one of air, water or iontophoretic device activation.

24. A method for treating, a disorder of an anatomical element comprising:
  (a) applying a combination exothermic heating and stimulating apparatus having a side for application to an anatomical element, the apparatus comprising:
    (i) a stimulating device for providing current stimulation of the anatomical element, wherein the stimulating device comprises:
      (a) a power supply for powering the stimulating device;
      (b) at least one positive electrode, connected to the power supply; and
      (c) at least one negative electrode, connected to the power supply, wherein the at least one electrodes are for conducting current to the anatomical element; and
    (ii) an exothermic heating component for heating the anatomical element, wherein the exothermic heating component is contacted with the side and is adapted to directly contact the anatomical element;
  (b) providing exothermic heating of the anatomical element; and
  (c) administering an active substance by iontophoresis to the anatomical element.

25. The method of claim 24, wherein the disorder is at least one of a dermatological disorder, a medical disorder, a disorder responsive to iontophoretic drug therapy and pain management.

26. The method of claim 24, wherein the treating is directed to a disease etiology selected from the group consisting of bacterial, fungal, viral, parasitic, inflammatory, autoimmune, allergic, hormonal, malignant and combinations thereof.

27. A combination exothermic heating and stimulating apparatus comprising:
  (a) a stimulating device for providing current stimulation of an anatomical element, wherein the stimulating device comprises: (i) a power supply for powering the stimulating device; (ii) at least one positive electrode, connected to the power supply; and (iii) at least one negative electrode, connected to the power supply, wherein the at least one electrodes are for conducting current to the anatomical element; and
  (b) an exothermic heating component for heating the anatomical element, wherein the exothermic heating component is contacted with a side of the apparatus for application to the anatomical element and is adapted to directly contact the anatomical element, and wherein the exothermic heating component is contacted with the stimulating device.

28. A combination exothermic heating and stimulating apparatus having a side for application to an anatomical element, the apparatus comprising:
  (a) a stimulating device for providing current stimulation of the anatomical element, wherein the stimulating device comprises: (i) a power supply for powering the stimulating device; (ii) at least one positive electrode, connected to the power supply; and (iii) at least one negative electrode, connected to the power supply, wherein the at least one electrodes are for conducting current to the anatomical element; and
  (b) an exothermic heat generating component for heating the anatomical element, wherein the exothermic heat generating component is directly contacted with the side for application to the anatomical element.

* * * * *